(12) United States Patent
Bhagwat et al.

(10) Patent No.: US 10,857,138 B2
(45) Date of Patent: Dec. 8, 2020

(54) PHARMACEUTICAL COMPOSITIONS COMPRISING ANTIBACTERIAL AGENTS

(71) Applicant: WOCKHARDT LIMITED, Maharashtra (IN)

(72) Inventors: Sachin Bhagwat, Aurangabad (IN); Snehal Rameshwar Palwe, Buldana (IN); Prashant Ratnakar Joshi, Parbhani (IN); Hemant Narendra Khande, Nashik (IN); Kushal Umarkar, Akola (IN); Mahesh Vithalbhai Patel, Aurangabad (IN)

(73) Assignee: WOCKHARDT LIMITED, Aurangabad (IN)

( * ) Notice: Subject to any disclaimer, the term of this patent is extended or adjusted under 35 U.S.C. 154(b) by 0 days.

(21) Appl. No.: 15/304,486

(22) PCT Filed: Apr. 17, 2015

(86) PCT No.: PCT/IB2015/052814
§ 371 (c)(1),
(2) Date: Oct. 14, 2016

(87) PCT Pub. No.: WO2015/159265
PCT Pub. Date: Oct. 22, 2015

(65) Prior Publication Data
US 2017/0035740 A1 Feb. 9, 2017

(30) Foreign Application Priority Data
Apr. 18, 2014 (IN) .......................... 1407/MUM/2014

(51) Int. Cl.
| | |
|---|---|
| *A61K 31/44* | (2006.01) |
| *A61K 31/397* | (2006.01) |
| *A61K 31/439* | (2006.01) |
| *A61K 45/06* | (2006.01) |
| *A61K 9/00* | (2006.01) |
| *A61K 31/427* | (2006.01) |
| *A61K 31/4545* | (2006.01) |

(52) U.S. Cl.
CPC .......... *A61K 31/439* (2013.01); *A61K 9/0095* (2013.01); *A61K 31/427* (2013.01); *A61K 31/4545* (2013.01); *A61K 45/06* (2013.01)

(58) Field of Classification Search
None
See application file for complete search history.

(56) References Cited

U.S. PATENT DOCUMENTS

2013/0225554 A1* 8/2013 Maiti .................. C07D 519/00
514/210.21
2013/0289012 A1* 10/2013 Gu .................. C07D 471/08
514/203

FOREIGN PATENT DOCUMENTS

| CA | 2 874 279 A1 | 12/2013 |
|---|---|---|
| WO | 2013/030733 A1 | 3/2013 |
| WO | 2013/038330 A1 | 3/2013 |
| WO | 2013/149121 A1 | 10/2013 |
| WO | 2014/108872 A1 | 7/2014 |

OTHER PUBLICATIONS

Medscape (Aztreonam) [online] Retrieved on Aug. 24, 2017 Retrieved from: <url:http://reference.medscape.com/drug/azactam-aztreonam-342553> Published on Jul. 6, 2013.*
Sugar et al., Interactions of Itraconazole with Amphotericin B in the Treatment of Murine Invasive Candidiasis. The Journal of Infectious Diseases 1988, vol. 177, pp. 1660-1663.
Maesaki et al. Effects of antifungal agent combinations administered simultaneously and sequentially against *Aspergillus fumigatus*. Antimicrobial Agents and Chemotherapy, Dec. 1994, pp. 2843-2845.
Bergogne-Berezin. Mechanisms and clinical relevance of antagonism between beta-lactam antibiotics. Chemioterapia. Feb. 1985;4(1):47-52.
Ventola. The Antibiotic Resistance Crisis. Part 1: Causes and Threats. P T. Apr. 2015; 40(4): 277-283.
Penchovsky. Designing drugs that overcome antibacterial resistance: where do we stand and what should we do? Expert Opin Drug Discov. Jun. 2015;1 (6):631-650.
Fleming. Penicillin Nobel Lecture, Dec. 11, 1945.
O'Neill. Tackling drug-resistant infections globally: final report and recommendations. the review on antimicrobial resistance May 2016. 84 pages.
Wanted: a reward for antibiotic development. Nature Biotechnology—vol. 36, No. 7 Jul. 2018, p. 555.

* cited by examiner

*Primary Examiner* — Shengjun Wang
(74) *Attorney, Agent, or Firm* — Bio Intellectual Property Services LLC (Bio IPS); O. (Sam) Zaghmout

(57) ABSTRACT

Pharmaceutical compositions comprising aztreonam or a pharmaceutically acceptable derivative, and a compound of Formula (I) or a stereoisomer or a pharmaceutically acceptable derivative thereof are disclosed. (I)

Formula (I)

13 Claims, No Drawings

PHARMACEUTICAL COMPOSITIONS COMPRISING ANTIBACTERIAL AGENTS

RELATED PATENT APPLICATIONS

This application claims priority to Indian Patent Application No. 1407/MUM/2014 filed on Apr. 18, 2014 the disclosures of which are incorporated herein by reference in its entirety as if fully rewritten herein.

FIELD OF THE INVENTION

The invention relates to antibacterial compositions and methods for treating or preventing bacterial infections.

BACKGROUND OF THE INVENTION

Bacterial infections continue to remain one of the major causes contributing towards human diseases. One of the key challenges in treatment of bacterial infections is the ability of bacteria to develop resistance to one or more antibacterial agents over time. Examples of such bacteria that have developed resistance to typical antibacterial agents include: Penicillin-resistant *Streptococcus pneumoniae*, Vancomycin-resistant Enterococci, and Methicillin-resistant *Staphylococcus aureus*. The problem of emerging drug-resistance in bacteria is often tackled by switching to newer antibacterial agents, which can be more expensive and sometimes more toxic. Additionally, this may not be a permanent solution as the bacteria often develop resistance to the newer antibacterial agents as well in due course. In general, bacteria are particularly efficient in developing resistance, because of their ability to multiply very rapidly and pass on the resistance genes as they replicate.

The persistent exposure of bacterial strains to a multitude of beta-lactam antibacterial agents has led to overproduction and mutation of beta-lactamases. These new extended spectrum beta-lactamases (ESBL) are capable of hydrolyzing penicillins, cephalosporins, monobactams and even carbapenems. Such a wide spread resistance to many of the existing beta-lactam antibacterial agents, either used alone or in combination with other agents, is posing challenges in treating serious bacterial infections.

Therefore, there is a need for development of newer ways to treat infections that are becoming resistant to known therapies and methods. Surprisingly, it has been found that a compositions comprising aztreonam and certain nitrogen containing bicyclic compounds exhibit unexpectedly synergistic antibacterial activity, even against highly resistant bacterial strains.

SUMMARY OF THE INVENTION

Accordingly, there are provided pharmaceutical compositions comprising: (a) aztreonam or a pharmaceutically acceptable derivative thereof, and (b) a compound of Formula (I) or a stereoisomer or a pharmaceutically acceptable derivative thereof:

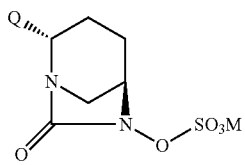

Formula (I)

wherein Q is:
(a) cyano,
(b) five to fourteen membered heteroaryl, optionally substituted with one or more of the following:
  (i) —CO—NH$_2$,
  (ii) five to fourteen membered heteroaryl,
  (iii) three to seven membered heterocycloalkyl,
  (iv) three to seven membered cycloalkyl,
  (v) five to fourteen membered aryl, or
  (vi) $C_1$-$C_6$ alkyl, optionally substituted with —NH$_2$ or three to seven membered heterocycloalkyl,
(c) —CO—NH—NH—CO—R$_1$, or
(d) —CO—NH—O—R$_1$;
R$_1$ is
(a) three to seven membered heterocycloalkyl, or
(b) $C_1$-$C_6$ alkyl, optionally substituted with three to seven membered heterocycloalkyl;
M is a cation.

In one general aspect, there are provided pharmaceutical compositions comprising: (a) aztreonam or a pharmaceutically acceptable derivative thereof, and (b) a compound of Formula (I) or a stereoisomer or a pharmaceutically acceptable derivative thereof; wherein a compound of Formula (I) or a stereoisomer or a pharmaceutically acceptable derivative thereof is present in the composition in an amount from about 0.01 gram to about 8 gram per gram of aztreonam or a pharmaceutically acceptable derivative thereof.

In yet another general aspect, there are provided methods for treating or preventing a bacterial infection in a subject, said methods comprising administering to said subject an effective amount of a pharmaceutical composition comprising: (a) aztreonam or a pharmaceutically acceptable derivative thereof; and (b) a compound of Formula (I) or a stereoisomer or a pharmaceutically acceptable derivative thereof.

In another general aspect, there are provided methods for treating or preventing a bacterial infection in a subject, said methods comprising administering to said subject an effective amount of a pharmaceutical composition comprising: (a) aztreonam or a pharmaceutically acceptable derivative thereof, and (b) a compound of Formula (I) or a stereoisomer or a pharmaceutically acceptable derivative thereof; wherein a compound of Formula (I) or a stereoisomer or a pharmaceutically acceptable derivative thereof is present in the composition in an amount from about 0.01 gram to about 8 gram per gram of aztreonam or a pharmaceutically acceptable derivative thereof.

In yet another general aspect, there are provided methods for treating or preventing a bacterial infection in a subject, said methods comprising administering to said subject an effective amount of: (a) aztreonam or a pharmaceutically acceptable derivative thereof; and (b) a compound of Formula (I) or a stereoisomer or a pharmaceutically acceptable derivative thereof.

In another general aspect, there are provided methods for treating or preventing a bacterial infection in a subject, said methods comprising administering to said subject an effective amount of: (a) aztreonam or a pharmaceutically acceptable derivative thereof, and (b) a compound of Formula (I) or a stereoisomer or a pharmaceutically acceptable derivative thereof; wherein a compound of Formula (I) or a stereoisomer or a pharmaceutically acceptable derivative thereof is administered in an amount from about 0.01 gram to about 8 gram per gram of aztreonam or a pharmaceutically acceptable derivative thereof.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification and the appended claims, the singular forms "a", "an", and "the" include plural referents unless the content clearly dictates otherwise. All references including patents, patent applications, and literature cited in the specification are expressly incorporated herein by reference in their entirety as if fully rewritten herein.

The inventors have surprisingly discovered that a pharmaceutical composition comprising: (a) aztreonam or a pharmaceutically acceptable derivative thereof, and (b) a compound of Formula (I) or a stereoisomer or a pharmaceutically acceptable derivative thereof exhibits unexpectedly improved antibacterial efficacy, even against highly resistant bacteria, including those producing extended spectrum beta-lactamase enzymes (ESBLs).

The term "$C_1$-$C_6$ alkyl" as used herein refers to branched or unbranched acyclic hydrocarbon radical with 1 to 6 carbon atoms. Typical, non-limiting examples of "$C_1$-$C_6$ alkyl" include methyl, ethyl, n-propyl, iso-propyl, n-butyl, iso-butyl, tert-butyl, n-pentyl, iso-pentyl, n-hexyl and the like. The "$C_1$-$C_6$ alkyl" may be unsubstituted, or substituted with one or more substituents. Typical, non-limiting examples of such substituents include halogen, alkoxy, CN, COOH, $CONH_2$, OH, $NH_2$, $NHCOCH_3$, cycloalkyl, heterocycloalkyl, heteroaryl, aryl and the like.

The term "heterocycloalkyl" as used herein refers to three to seven member cycloalkyl group containing one or more heteroatoms selected from nitrogen, oxygen or sulfur. The heterocycloalkyl group optionally incorporates one or more double or triple bonds, or a combination of double bonds and triple bonds, but which is not aromatic. Typical, non-limiting examples of heterocycloalkyl groups include pyrrolidine, 2-oxo-pyrrolidine, imidazolidin-2-one, piperidine, oxazine, thiazine, piperazine, piperazin-2,3-dione, morpholine, thiamorpholine, azapane, and the like. The heterocycloalkyl may be unsubstituted, or substituted with one or more substituents. Typical, non-limiting examples of such substituents include $C_1$-$C_6$ alkyl, halogen, alkoxy, CN, COOH, $CONH_2$, OH, $NH_2$, $NHCOCH_3$, heterocyclyl, heteroaryl, aryl, $SO_2$-alkyl, $SO_2$-aryl, $OSO_2$-alkyl, $OSO_2$-aryl and the like. The term "heterocyclyl" as used herein refers to cyclic groups in which a ring portion includes at least one heteroatom such as oxygen, nitrogen or sulfur. Heterocyclic groups include "heteroaryl" as well as "heterocycloalkyl".

The term "cycloalkyl" as used herein refers to three to seven member cyclic hydrocarbon radicals. The cycloalkyl group optionally incorporates one or more double or triple bonds, or a combination of double bonds and triple bonds, but which is not aromatic. Typical, non-limiting examples of cycloalkyl groups include cyclopropyl, cyclobutyl, cyclopentyl, cyclohexyl, cycloheptyl. The cycloalkyl may be unsubstituted, or substituted with one or more substituents. Typical, non-limiting examples of such substituents include $C_1$-$C_6$ alkyl, halogen, alkoxy, CN, COOH, $CONH_2$, OH, $NH_2$, $NHCOCH_3$, heterocyclyl, heteroaryl, aryl, $SO_2$-alkyl, $SO_2$-aryl, $OSO_2$-alkyl, $OSO_2$-aryl and the like.

The term "aryl" as used herein refers to a monocyclic or polycyclic aromatic hydrocarbon. Typical, non-limiting examples of aryl groups include phenyl, naphthyl, anthracenyl, fluorenyl, phenanthrenyl, and the like. The aryl group may be unsubstituted, or substituted with one or more substitutents. Typical, non-limiting examples of such substituents include $C_1$-$C_6$ alkyl, halogen, alkoxy, CN, COOH, $CONH_2$, OH, $NH_2$, $NHCOCH_3$, heterocyclyl, heteroaryl, aryl, $SO_2$-alkyl, $SO_2$-aryl, $OSO_2$-alkyl, $OSO_2$-aryl and the like. In some embodiments, the term "aryl" refers to five to fourteen membered monocyclic or polycyclic aromatic hydrocarbon radical.

The term "heteroaryl" as used herein refers to a monocyclic or polycyclic aromatic hydrocarbon group wherein one or more carbon atoms have been replaced with heteroatoms selected from nitrogen, oxygen or sulfur. If the heteroaryl group contains more than one heteroatom, the heteroatoms may be same or different. Typical non-limiting examples of heteroaryl group include 1,2,4-oxadiazole, 1,3,4-oxadiazole, 1,3,4-thiadiazole, 1,2,3,4-tetrazole, 1,3-oxazole, 1,3-thiazole, pyridine, pyrimidine, pyrazine, pyridazine, furan, pyrrol, thiophene, imidazole, and the like. In some embodiments, the term "heteroaryl" refers to five to fourteen membered monocyclic or polycyclic aromatic hydrocarbon radical.

The term "infection" or "bacterial infection" as used herein includes presence of bacteria, in or on a subject, which, if its growth were inhibited, would result in a benefit to the subject. As such, the term "infection" in addition to referring to the presence of bacteria also refers to presence of other floras, which are not desirable. The term "infection" includes infection caused by bacteria.

The term "treat", "treating" or "treatment" as used herein refers to administration of a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions, or one or more of pharmaceutically active ingredients discussed herein, with or without additional pharmaceutically active or inert ingredients, in order to: (i) reduce or eliminate either a bacterial infection, or one or more symptoms of a bacterial infection, or (ii) retard progression of a bacterial infection, or one or more symptoms of a bacterial infection, or (iii) reduce severity of a bacterial infection, or one or more symptoms of a bacterial infection, or (iv) suppress clinical manifestation of a bacterial infection, or (v) suppress manifestation of adverse symptoms of a bacterial infection.

The terms "pharmaceutically effective amount" or "therapeutically effective amount" or "effective amount" as used herein refer to an amount, which has a therapeutic effect or is the amount required to produce a therapeutic effect in a subject. For example, a "therapeutically effective amount" or "pharmaceutically effective amount" or "effective amount" of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g.

in agar or broth media). Such effective amount depends on several factors, including but not limited to, the microorganism (e.g. bacteria) involved, characteristics of the subject (for example height, weight, sex, age and medical history), severity of infection and particular type of the antibacterial agent used. For prophylactic treatments, a prophylactically effective amount is that amount which would be effective in preventing the bacterial infection.

The term "administration" or "administering" refers to and includes delivery of a composition, or one or more pharmaceutically active ingredients to a subject, including for example, by any appropriate method, which serves to deliver the composition or its active ingredients or other pharmaceutically active ingredients to the site of infection. The method of administration may vary depending on various factors, such as for example, the components of the pharmaceutical composition or type/nature of the pharmaceutically active or inert ingredients, site of the potential or actual infection, the microorganism involved, severity of the infection, age and physical condition of the subject and a like. Some non-limiting examples of ways to administer a composition or a pharmaceutically active ingredient to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop and mouthwash. In case of a pharmaceutical composition comprising more than one ingredients (active or inert), one of the ways of administering such composition is by admixing the ingredients (e.g. in the form of a suitable unit dosage form such as tablet, capsule, solution, powder or a like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "growth" as used herein refers to a growth of one or more microorganisms and includes reproduction or population expansion of the microorganism (e.g. bacteria). The term "growth" also includes maintenance of on-going metabolic processes of the microorganism, including the processes that keep the microorganism alive.

The term, "effectiveness" as used herein refers to ability of a treatment, or a composition, or one or more pharmaceutically active ingredients to produce a desired biological effect in a subject. For example, the term "antibacterial effectiveness" of a composition or of an antibacterial agent refers to the ability of the composition or the antibacterial agent to prevent or treat bacterial infection in a subject.

The term "synergistic" or "synergy" as used herein refers to the interaction of two or more agents so that their combined effect is greater than their individual effects.

The term "antibacterial agent" as used herein refers to any substance, compound, a combination of substances, or a combination of compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "beta-lactam antibacterial agent" as used herein refers to compounds with antibacterial properties and containing a beta-lactam nucleus in their molecular structure.

The term "beta-lactamase" or "beta-lactamase enzyme" as used herein refers to any enzyme or protein or any other substance that breaks down a beta-lactam ring. The term "beta-lactamase" includes enzymes that are produced by bacteria and have the ability to hydrolyse the beta-lactam ring in a beta-lactam compound, either partially or completely.

The term "extended spectrum beta-lactamase" (ESBL) as used herein includes those beta-lactamase enzymes, which are capable of conferring bacterial resistance to various beta-lactam antibacterial agents such as penicillins, cephalosporins, aztreonam and the like.

The term "beta-lactamase inhibitor" as used herein refers to a compound capable of inhibiting activity of one or more beta-lactamase enzymes, either partially or completely.

The term "colony forming units" or "CFU" as used herein refers to an estimate of number of viable bacterial cells per ml of the sample. Typically, a "colony of bacteria" refers to a mass of individual bacteria growing together.

The term "pharmaceutically inert ingredient" or "carrier" or "excipient" refers to and includes compounds or materials used to facilitate administration of a compound, for example, to increase the solubility of the compound. Typical, non-limiting examples of solid carriers include starch, lactose, dicalcium phosphate, sucrose, and kaolin. Typical, non-limiting examples of liquid carriers include sterile water, saline, buffers, non-ionic surfactants, and edible oils. In addition, various adjuvants commonly used in the art may also be included. These and other such compounds are described in literature, e.g., in the Merck Index (Merck & Company, Rahway, N.J.). Considerations for inclusion of various components in pharmaceutical compositions are described, e.g., in Gilman et al. (Goodman and Gilman's: The Pharmacological Basis of Therapeutics, 8th Ed., Pergamon Press., 1990), which is incorporated herein by reference in its entirety.

The term "subject" as used herein refers to vertebrate or invertebrate, including a mammal. The term "subject" includes human, animal, a bird, a fish, or an amphibian. Typical, non-limiting examples of a "subject" include humans, cats, dogs, horses, sheep, bovine cows, pigs, lambs, rats, mice and guinea pigs.

The term "pharmaceutically acceptable derivative" as used herein refers to and includes any pharmaceutically acceptable salt, pro-drug, metabolite, ester, ether, hydrate, polymorph, solvate, complex, and adduct of a compound described herein which, upon administration to a subject, is capable of providing (directly or indirectly) the parent compound. For example, the term "antibacterial agent or a pharmaceutically acceptable derivative thereof" includes all derivatives of the antibacterial agent (such as salts, pro-drugs, metabolites, esters, ethers, hydrates, polymorphs, solvates, complexes, and adducts) which, upon administration to a subject, are capable of providing (directly or indirectly) the antibacterial agent.

The term "pharmaceutically acceptable salt" as used herein refers to one or more salts of a given compound which possesses desired pharmacological activity of the free compound and which is neither biologically nor otherwise undesirable. In general, the term "pharmaceutically acceptable salts" refer to salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (*J. Pharmaceutical Sciences*, 66; 1-19, 1977), incorporated herein by reference in its entirety, describes various pharmaceutically acceptable salts in details.

A reference to aztreonam is intended to include its pharmaceutically acceptable salts, pro-drugs, metabolites, esters, ethers, hydrates, polymorphs, solvates, complexes, enantiomers, adducts and its any other pharmaceutically acceptable derivative.

The term "stereoisomer" as used herein refers to and includes isomeric molecules that have the same molecular formula but differ in positioning of atoms and/or functional groups in the space. Stereoisomers may further be classified as enantiomers (where different isomers are mirror-images of each other) and diastereomers (where different isomers are not mirror-images of each other). Diastereomers include isomers such as conformers, meso compounds, cis-trans (E-Z) isomers, and non-enantiomeric optical isomers.

A person of skills in the art would appreciate that various compounds described herein (including, for example a compound of Formula (I) and aztreonam) can exist and are often used as their pharmaceutically acceptable derivatives (such as salts, pro-drugs, metabolites, esters, ethers, hydrates, polymorphs, solvates, complexes, and adducts).

In one general aspect, there are provided pharmaceutical compositions comprising: (a) aztreonam or a pharmaceutically acceptable derivative thereof, and (b) a compound of Formula (I) or a stereoisomer or a pharmaceutically acceptable derivative thereof:

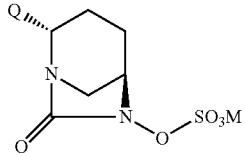

Formula (I)

wherein Q is:
(a) cyano,
(b) five to fourteen membered heteroaryl, optionally substituted with one or more of the following:
  (i) —CO—NH$_2$,
  (ii) five to fourteen membered heteroaryl,
  (iii) three to seven membered heterocycloalkyl,
  (iv) three to seven membered cycloalkyl,
  (v) five to fourteen membered aryl, or
  (vi) C$_1$-C$_6$ alkyl, optionally substituted with —NH$_2$ or three to seven membered heterocycloalkyl,
(c) —CO—NH—NH—CO—R$_1$, or
(d) —CO—NH—O—R$_1$;
R$_1$ is
(a) three to seven membered heterocycloalkyl, or
(b) C$_1$-C$_6$ alkyl, optionally substituted with three to seven membered heterocycloalkyl;
M is a cation.

In general, the term "cation" includes H, Na, K, Mg, Ca, NH$_4^+$, (CH$_3$CH$_2$)$_3$N$^+$ and a like.

In some embodiments, compound of Formula (I) is selected from:
(a) trans-7-oxo-6-(sulphooxy)-1,6-diazabicyclo[3.2.1]-octane-2-carbonitrile;
(b) trans-sulphuric acid mono-[2-(5-carboxamido)-[1,3,4]-oxadiazol-2-yl)-7-oxo-1,6-diazabicyclo[3.2.1]-octan-6-yl] ester;
(c) trans-sulphuric acid mono-[2-(5-(piperidin-4-yl)-[1,3,4]-oxadiazol-2-yl)-7-oxo-1,6-diazabicyclo[3.2.1]-octan-6-yl] ester;
(d) trans-sulphuric acid mono-[2-(5-azetidin-3-ylmethyl-[1,3,4]-oxadiazol-2-yl)-7-oxo-1,6-diazabicyclo[3.2.1]-octan-6-yl] ester;
(e) (2S,5R)-7-oxo-6-sulphooxy-2-[N'—((R)-piperidine-3-carbonyl)-hydrazino carbonyl]-1,6-diaza-bicyclo[3.2.1]octane;
(f) (2S,5R)-7-oxo-N-[(2S)-pyrrolidin-2-ylmethoxy]-6-(sulfooxy)-1,6-diaza bicyclo[3.2.1]octane-2-carboxamide;
(g) (2S,5R)-7-oxo-6-sulphooxy-2-[N'—((R)-pyrrolidine-3-carbonyl)-hydrazinocarbonyl]-1,6-diaza-bicyclo[3.2.1]octane;
(h) (2S,5R)-7-oxo-N-[(2S)-piperidine-2-ylmethyloxy]-6-(sulfooxy)-1,6-diazabicyclo[3.2.1]octane-2-carboxamide;
(i) trans-sulphuric acid mono-[2-(5-((S)-1-amino-ethyl)-[1,3,4]-oxadiazol-2-yl)-7-oxo-1,6-diazabicyclo[3.2.1]-octan-6-yl] ester;
(j) trans-sulphuric acid mono-[2-(5-((S)-pyrrolidin-2-yl)-[1,3,4]-oxadiazol-2-yl)-7-oxo-1,6-diazabicyclo[3.2.1]-octan-6-yl] ester;
or a stereoisomer or a pharmaceutically acceptable derivative thereof.

Compound of Formula (I), according to the invention can be used in various forms including as such, a stereoisomer or a pharmaceutically acceptable derivative thereof. Compound of Formula (I) may also be used in the form of its stereoisomer or a pharmaceutically acceptable derivative thereof. Typical, non-limiting examples of suitable pharmaceutically acceptable derivatives of a compound of Formula (I) include its sodium salt and potassium salt.

In another general aspect, there are provided pharmaceutical compositions comprising: (a) aztreonam or a pharmaceutically acceptable derivative thereof, and (b) a compound of Formula (I) or a stereoisomer or a pharmaceutically acceptable derivative thereof; wherein a compound of Formula (I) or a stereoisomer or a pharmaceutically acceptable derivative thereof is present in the composition in an amount from about 0.01 gram to about 8 gram per gram of aztreonam or a pharmaceutically acceptable derivative thereof.

Both, aztreonam and a compound of Formula (I) may be present in the composition in their free forms or in the form of their pharmaceutically acceptable derivatives (such as salts, pro-drugs, metabolites, esters, ethers, hydrates, polymorphs, solvates, complexes, or adducts). The specified ratio of aztreonam and compound of Formula (I) in the composition is calculated on the basis of their free forms. For example, if the composition comprises sodium salt of compound of Formula (I), the ratio of aztreonam to compound of Formula (I) is calculated using the equivalent amount of compound of Formula (I) present in the composition.

Individual amounts of a compound of Formula (I) or a stereoisomer or a pharmaceutically acceptable derivative thereof, and aztreonam or a pharmaceutically acceptable derivative thereof in the composition may vary depending on clinical requirements. In some embodiments, a compound of Formula (I) or a stereoisomer or a pharmaceutically acceptable derivative thereof in the composition is present in an amount from about 0.01 gram to about 10 gram. In some other embodiments, aztreonam or a pharmaceutically acceptable derivative thereof in the composition is present in an amount from about 0.01 gram to about 10 gram.

In some embodiments, the pharmaceutical composition according to the invention comprises about 0.25 gram of a compound of Formula (I) or a stereoisomer or a pharmaceutically acceptable derivative thereof, and about 0.5 gram of aztreonam or a pharmaceutically acceptable derivative thereof.

In some other embodiments, the pharmaceutical composition according to the invention comprises about 0.5 gram of a compound of Formula (I) or a stereoisomer or a pharmaceutically acceptable derivative thereof, and about 0.5 gram of aztreonam or a pharmaceutically acceptable derivative thereof.

In some embodiments, the pharmaceutical composition according to the invention comprises about 1 gram of a compound of Formula (I) or a stereoisomer or a pharmaceutically acceptable derivative thereof, and about 0.5 gram of aztreonam or a pharmaceutically acceptable derivative thereof.

In some embodiments, the pharmaceutical composition according to the invention comprises about 2 gram of a compound of Formula (I) or a stereoisomer or a pharmaceutically acceptable derivative thereof, and about 0.5 gram of aztreonam or a pharmaceutically acceptable derivative thereof.

In some other embodiments, the pharmaceutical composition according to the invention comprises about 0.25 gram of a compound of Formula (I) or a stereoisomer or a pharmaceutically acceptable derivative thereof, and about 1 gram of aztreonam or a pharmaceutically acceptable derivative thereof.

In some embodiments, the pharmaceutical composition according to the invention comprises about 0.5 gram of a compound of Formula (I) or a stereoisomer or a pharmaceutically acceptable derivative thereof, and about 1 gram of aztreonam or a pharmaceutically acceptable derivative thereof.

In some embodiments, the pharmaceutical composition according to the invention comprises about 1 gram of a compound of Formula (I) or a stereoisomer or a pharmaceutically acceptable derivative thereof, and about 1 gram of aztreonam or a pharmaceutically acceptable derivative thereof.

In some embodiments, the pharmaceutical composition according to the invention comprises about 2 gram of a compound of Formula (I) or a stereoisomer or a pharmaceutically acceptable derivative thereof, and about 1 gram of aztreonam or a pharmaceutically acceptable derivative thereof.

In some embodiments, the pharmaceutical composition according to the invention comprises about 4 gram of a compound of Formula (I) or a stereoisomer or a pharmaceutically acceptable derivative thereof, and about 1 gram of aztreonam or a pharmaceutically acceptable derivative thereof.

In some embodiments, the pharmaceutical composition according to the invention comprises about 2 gram of a compound of Formula (I) or a stereoisomer or a pharmaceutically acceptable derivative thereof, and about 2 gram of aztreonam or a pharmaceutically acceptable derivative thereof.

In some other embodiments, the pharmaceutical composition according to the invention comprises about 1 gram of a compound of Formula (I) or a stereoisomer or a pharmaceutically acceptable derivative thereof, and about 2 gram of aztreonam or a pharmaceutically acceptable derivative thereof.

In some embodiments, there is provided a pharmaceutical composition comprising (a) aztreonam or a pharmaceutically acceptable derivative thereof, and (b) sodium salt of trans-7-oxo-6-sulphooxy-1,6-diazabicyclo[3.2.1]-octane-2-carbonitrile or a stereoisomer thereof.

In some embodiments, there is provided a pharmaceutical composition comprising (a) aztreonam or a pharmaceutically acceptable derivative thereof, and (b) trans-sulphuric acid mono-[2-(5-carboxamido)-[1,3,4]-oxadiazol-2-yl)-7-oxo-1,6-diazabicyclo[3.2.1]-octan-6-yl] ester In some embodiments, there is provided a comprising (a) aztreonam or a pharmaceutically acceptable derivative thereof, and (b) trans-sulphuric acid mono-[2-(5-(piperidin-4-yl)-[1,3,4]-oxadiazol-2-yl-7-oxo-1,6-diazabicyclo[3.2.1]-octan-6-yl] ester or a stereoisomer or a pharmaceutically acceptable derivative thereof.

In some embodiments, there is provided a pharmaceutical composition comprising (a) aztreonam or a pharmaceutically acceptable derivative thereof, and (b) trans-sulphuric acid mono-[2-(5-azetidin-3-ylmethyl-[1,3,4]-oxadiazol-2-yl)-7-oxo-1,6-diazabicyclo[3.2.1]-octan-6-yl] ester or a stereoisomer or a pharmaceutically acceptable derivative thereof.

In some embodiments, there is provided a pharmaceutical composition comprising (a) aztreonam or a pharmaceutically acceptable derivative thereof, and (b) (2S,5R)-7-oxo-6-sulphooxy-2-[N'—((R)-piperidine-3-carbonyl)-hydrazinocarbonyl]-1,6-diaza-bicyclo[3.2.1]octane or a stereoisomer or a pharmaceutically acceptable derivative thereof.

In some embodiments, there is provided a composition comprising (a) aztreonam or a pharmaceutically acceptable derivative thereof, and (b) (2S,5R)-7-Oxo-N-[(2S)-pyrrolidin-2-ylmethoxy]-6-(sulfooxy)-1,6-diaza bicyclo[3.2.1]octane-2-carboxamide or a stereoisomer or a pharmaceutically acceptable derivative thereof.

In some embodiments, there is provided a pharmaceutical composition comprising (a) aztreonam or a pharmaceutically acceptable derivative thereof, and (b) (2S,5R)-7-Oxo-6-sulphooxy-2-[N'—((R)-pyrrolidine-3-carbonyl)-hydrazinocarbonyl]-1,6-diaza-bicyclo[3.2.1]octane or a stereoisomer or a pharmaceutically acceptable derivative thereof.

In some embodiments, there is provided a pharmaceutical composition comprising (a) aztreonam or a pharmaceutically acceptable derivative thereof, and (b) (2S,5R)-7-Oxo-N-[(2S)-piperidine-2-ylmethyloxy]-6-(sulfooxy)-1,6-diazabicyclo[3.2.1]octane-2-carboxamide or a stereoisomer or a pharmaceutically acceptable derivative thereof.

In some embodiments, there is provided a comprising (a) aztreonam or a pharmaceutically acceptable derivative thereof, and (b) trans-sulphuric acid mono-[2-(5-((S)-1-amino-ethyl)-[1,3,4]-oxadiazol-2-yl)-7-oxo-1,6-diazabicyclo[3.2.1]-octan-6-yl] ester or a stereoisomer or a pharmaceutically acceptable derivative thereof.

In some embodiments, there is provided a pharmaceutical composition comprising (a) aztreonam or a pharmaceutically acceptable derivative thereof, and (b) trans-sulphuric acid mono-[2-(5-((S)-pyrrolidin-2-yl)-[1,3,4]-oxadiazol-2-yl)-7-oxo-1,6-diazabicyclo[3.2.1]-octan-6-yl] ester or a stereoisomer or a pharmaceutically acceptable derivative thereof.

The pharmaceutical compositions according to the invention may include one or more pharmaceutically acceptable carriers or excipients or the like. Typical, non-limiting examples of such carriers or excipients include mannitol, lactose, starch, magnesium stearate, sodium saccharine, talcum, cellulose, sodium crosscarmellose, glucose, gelatine, sucrose, magnesium carbonate, wetting agents, emulsifying agents, solubilizing agents, buffering agents, lubricants, preservatives, stabilizing agents, binding agents and the like. In some embodiments, the compositions according to present invention comprise arginine or a pharmaceutically acceptable salt thereof. The amount of arginine or a pharmaceutically acceptable salt thereof in the composition can vary widely depending on the requirement. In some embodiments, arginine or a pharmaceutically acceptable salt thereof is present in the composition in an amount of about 0.01 gram to about 5 gram of arginine or a pharmaceutically acceptable salt thereof per gram of aztreonam or a pharmaceutically acceptable salt thereof. In some other embodiments, arginine or a pharmaceutically acceptable salt thereof is present in the composition in an amount of about 0.01 gram to about 1 gram of arginine or a pharmaceutically acceptable salt thereof per gram of aztreonam or a pharmaceutically acceptable salt thereof.

The pharmaceutical compositions or the active ingredients according to the present invention may be formulated into a variety of dosage forms, such as solid, semi-solid, liquid and aerosol dosage forms. Typical, non-limiting examples of some dosage forms include tablets, capsules, powders, solutions, suspensions, suppositories, aerosols, granules, emulsions, syrups, elixirs and the like.

In some embodiments, pharmaceutical compositions according to the invention are in the form of a powder or a solution. In some other embodiments, pharmaceutical compositions according to the invention are present in the form of a powder or a solution that can be reconstituted by addition of a compatible reconstitution diluent prior to administration. In some other embodiments, pharmaceutical compositions according to the invention are in the form of a frozen composition that can be diluted with a compatible reconstitution diluent prior to administration. Typical, non-limiting example of suitable compatible reconstitution diluent includes water.

In some other embodiments, pharmaceutical compositions according to the invention are present in the form ready to use for parenteral administration.

The compositions according to the invention can be formulated into various dosage forms wherein the active ingredients and/or excipients may be present either together (e.g. as an admixture) or as separate components. When the various ingredients in the composition are formulated as a mixture, such compositions can be delivered by administering such a mixture to a subject using any suitable route of administration. Alternatively, pharmaceutical compositions according to the invention may also be formulated into a dosage form wherein one or more ingredients (such as active or inactive ingredients) are present as separate components. The composition or dosage form wherein the ingredients do not come as a mixture, but come as separate components, such composition/dosage form may be administered in several ways. In one possible way, the ingredients may be mixed in the desired proportions and the mixture is reconstituted in suitable reconstitution diluent and is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

In some embodiments, pharmaceutical compositions according to the invention are formulated into a dosage form such that a compound of Formula (I) or a stereoisomer or a pharmaceutically acceptable derivative thereof, and aztreonam or a pharmaceutically acceptable derivative thereof, are present in the composition as admixture or as separate components. In some other embodiments, pharmaceutical compositions according to the invention are formulated into a dosage form such that a compound of Formula (I) or a stereoisomer or a pharmaceutically acceptable derivative thereof, and aztreonam or a pharmaceutically acceptable derivative thereof, are present in the composition as separate components.

In one general aspect, pharmaceutical compositions according to the invention are used in treatment or prevention of a bacterial infection.

In another general aspect, there are provided methods for treating or preventing a bacterial infection in a subject, said method comprising administering to said subject effective amount of a pharmaceutical composition according to the invention. In case of dosage forms wherein a compound of Formula (I) or a stereoisomer or a pharmaceutically acceptable derivative thereof, and aztreonam or a pharmaceutically acceptable derivative thereof, are present in the composition as separate components; a compound of Formula (I) or a stereoisomer or a pharmaceutically acceptable derivative thereof may be administered before, after or simultaneously with the administration of aztreonam or a pharmaceutically acceptable derivative thereof.

In yet another general aspect, there are provided methods for treating or preventing bacterial infections in a subject, said methods comprising administering to said subject an effective amount of: (a) aztreonam or a pharmaceutically acceptable derivative thereof, and (b) a compound of Formula (I) or a stereoisomer or a pharmaceutically acceptable derivative thereof:

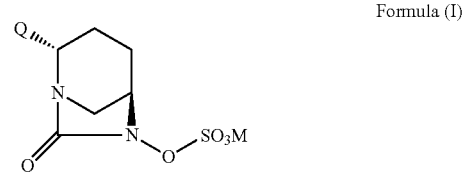

Formula (I)

wherein Q is:
(a) cyano,
(b) five to fourteen membered heteroaryl, optionally substituted with one or more of the following:
  (i) —CO—NH$_2$,
  (ii) five to fourteen membered heteroaryl,
  (iii) three to seven membered heterocycloalkyl,
  (iv) three to seven membered cycloalkyl,
  (v) five to fourteen membered aryl, or
  (vi) C$_1$-C$_6$ alkyl, optionally substituted with —NH$_2$ or three to seven membered heterocycloalkyl,
(c) —CO—NH—NH—CO—R$_1$, or
(d) —CO—NH—O—R$_1$;
R$_1$ is
(a) three to seven membered heterocycloalkyl, or
(b) C$_1$-C$_6$ alkyl, optionally substituted with three to seven membered heterocycloalkyl;
M is a cation.

In another general aspect, there are provided methods for treating or preventing bacterial infections in a subject, said methods comprising administering to said subject an effective amount of: (a) aztreonam or a pharmaceutically acceptable derivative thereof, and (b) a compound of Formula (I) or a stereoisomer or a pharmaceutically acceptable derivative thereof; wherein amount of a compound of Formula (I) or a stereoisomer or a pharmaceutically acceptable derivative thereof administered is from about 0.01 gram to about 8 gram per gram of aztreonam or a pharmaceutically acceptable derivative thereof.

In some embodiments, there is provided a method for treating or preventing a bacterial infection in a subject, said method comprising administering to said subject: (a) aztreonam or a pharmaceutically acceptable derivative thereof, and (b) a compound of Formula (I) or a stereoisomer or a pharmaceutically acceptable derivative thereof, in any of the following amounts:

(i) about 0.25 gram of a compound of Formula (I) or a stereoisomer or a pharmaceutically acceptable derivative thereof, and about 0.5 gram of aztreonam or a pharmaceutically acceptable derivative thereof;

(ii) about 0.5 gram of a compound of Formula (I) or a stereoisomer or a pharmaceutically acceptable derivative thereof, and about 0.5 gram of aztreonam or a pharmaceutically acceptable derivative thereof;

(iii) about 1 gram of a compound of Formula (I) or a stereoisomer or a pharmaceutically acceptable derivative thereof, and about 0.5 gram of aztreonam or a pharmaceutically acceptable derivative thereof;

(iv) about 2 gram of a compound of Formula (I) or a stereoisomer or a pharmaceutically acceptable derivative thereof, and about 0.5 gram of aztreonam or a pharmaceutically acceptable derivative thereof;

(v) about 0.25 gram of a compound of Formula (I) or a stereoisomer or a pharmaceutically acceptable derivative thereof, and about 1 gram of aztreonam or a pharmaceutically acceptable derivative thereof;

(vi) about 0.5 gram of a compound of Formula (I) or a stereoisomer or a pharmaceutically acceptable derivative thereof, and about 1 gram of aztreonam or a pharmaceutically acceptable derivative thereof;

(vii) about 1 gram of a compound of Formula (I) or a stereoisomer or a pharmaceutically acceptable derivative thereof, and about 1 gram of aztreonam or a pharmaceutically acceptable derivative thereof;

(viii) about 2 gram of a compound of Formula (I) or a stereoisomer or a pharmaceutically acceptable derivative thereof, and about 1 gram of aztreonam or a pharmaceutically acceptable derivative thereof;

(ix) about 4 gram of a compound of Formula (I) or a stereoisomer or a pharmaceutically acceptable derivative thereof, and about 1 gram of aztreonam or a pharmaceutically acceptable derivative thereof;

(x) about 2 gram of a compound of Formula (I) or a stereoisomer or a pharmaceutically acceptable derivative thereof, and about 2 gram of aztreonam or a pharmaceutically acceptable derivative thereof; or (xi) about 1 gram of a compound of Formula (I) or a stereoisomer or a pharmaceutically acceptable derivative thereof, and about 2 gram of aztreonam or a pharmaceutically acceptable derivative thereof.

In some embodiments, in the methods according to the invention, a compound of Formula (I) or a stereoisomer or a pharmaceutically acceptable derivative thereof is administered in an amount from about 0.01 gram to about 10 gram. In some other embodiments, in the methods according to the invention, aztreonam or a pharmaceutically acceptable derivative thereof is administered in an amount from about 0.01 gram to about 10 gram.

In some embodiments, in the methods according to the invention, a compound of Formula (I) or a stereoisomer or a pharmaceutically acceptable derivative thereof is administered before, after or simultaneously with the administration of aztreonam or a pharmaceutically acceptable derivative thereof.

In the methods according to the invention, the pharmaceutical composition and/or other pharmaceutically active ingredients disclosed herein may be administered by any appropriate method, which serves to deliver the composition, or its constituents, or the active ingredients to the desired site. The method of administration can vary depending on various factors, such as for example, the components of the pharmaceutical composition and the nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In some embodiments, the compositions or one or more active ingredients according to the invention are administered parenterally or orally.

In some embodiments, in the compositions and methods according to the invention, a compound of Formula (I) is trans-7-oxo-6-(sulphooxy)-1,6-diazabicyclo[3.2.1]-octane-2-carbonitrile; trans-sulphuric acid mono-[2-(5-carboxamido)-[1,3,4]-oxadiazol-2-yl)-7-oxo-1,6-diazabicyclo [3.2.1]-octan-6-yl] ester; trans-sulphuric acid mono-[2-(5-(piperidin-4-yl)-[1,3,4]-oxadiazol-2-yl)-7-oxo-1,6-diazabicyclo[3.2.1]-octan-6-yl] ester; trans-sulphuric acid mono-[2-(5-azetidin-3-ylmethyl-[1,3,4]-oxadiazol-2-yl)-7-oxo-1,6-diazabicyclo[3.2.1]-octan-6-yl] ester; (2S,5R)-7-oxo-6-sulphooxy-2-[N'—((R)-piperidine-3-carbonyl)-hydrazino carbonyl]-1,6-diaza-bicyclo[3.2.1]octane; (2S,5R)-7-oxo-N-[(2S)-pyrrolidin-2-ylmethoxy]-6-(sulfooxy)-1,6-diaza bicyclo[3.2.1]octane-2-carboxamide; (2S,5R)-7-Oxo-6-sulphooxy-2-[N'—((R)-pyrrolidine-3-carbonyl)-hydrazinocarbonyl]-1,6-diaza-bicyclo[3.2.1]octane; (2S, 5R)-7-oxo-N-[(2S)-piperidine-2-ylmethyloxy]-6-(sulfooxy)-1,6-diazabicyclo[3.2.1]octane-2-carboxamide; trans-sulphuric acid mono-[2-(5-((S)-1-amino-ethyl)-[1,3,4]-oxadiazol-2-yl)-7-oxo-1,6-diazabicyclo[3.2.1]-octan-6-yl] ester; trans-sulphuric acid mono-[2-(5-((S)-pyrrolidin-2-yl)-[1,3,4]-oxadiazol-2-yl)-7-oxo-1,6-diazabicyclo[3.2.1]-octan-6-yl] ester; or a stereoisomer or a pharmaceutically acceptable derivative thereof.

In some embodiments, in compositions and methods according to the invention, a compound of Formula (I) or a stereoisomer thereof is present as a sodium or potassium salt.

In some embodiments, there is provided a method for increasing antibacterial effectiveness of aztreonam or a pharmaceutically acceptable derivative thereof in a subject, said method comprising co-administering aztreonam or a pharmaceutically acceptable derivative thereof, with a compound of Formula (I) or a stereoisomer or a pharmaceutically acceptable derivative thereof. In some other embodiments, there is provided a method for increasing antibacterial effectiveness of aztreonam or a pharmaceutically acceptable derivative thereof in a subject, said method comprising co-administering aztreonam or a pharmaceutically acceptable derivative thereof, with a compound of Formula (I) or a stereoisomer or a pharmaceutically acceptable derivative thereof, wherein the amount of a compound of Formula (I) or a stereoisomer or a pharmaceutically acceptable derivative thereof is from about 0.01 gram to about 8 gram per gram of aztreonam or a pharmaceutically acceptable derivative thereof.

A wide variety of bacterial infections can be treated or prevented using compositions and methods according to the invention. Typical, non-limiting examples of bacterial infections that can be treated or prevented using methods and/or pharmaceutical compositions according to the invention include *E. coli* infections, *Yersinia pestis* (pneumonic plague), staphylococcal infection, mycobacteria infection, bacterial pneumonia, *Shigella* dysentery, *Serratia* infections, *Candida* infections, *Cryptococcal* infection, anthrax, tuberculosis or infections caused by *Pseudomonas aeruginosa, Acinetobacter baumannii* or methicillin resistant *Staphylococcus aurues* (MRSA) etc.

The pharmaceutical compositions and methods according to the invention are useful in treatment or prevention of several infections, including for example, skin and soft tissue infections, febrile neutropenia, urinary tract infection, intraabdominal infections, respiratory tract infections, pneumonia (nosocomial), bacteremia meningitis, surgical infections and the like.

In some embodiments, pharmaceutical compositions and methods according to the invention are used in treatment or prevention of infections caused by resistant bacteria. In some other embodiments, the compositions and methods according to the invention are used in treatment or prevention of infections caused by bacteria producing one or more beta-lactamase enzymes.

In general, the pharmaceutical compositions and methods disclosed herein are also effective in preventing or treating infections caused by bacteria that are considered to be less or not susceptible to one or more of known antibacterial agents or their known compositions. Some non-limiting examples of such bacteria known to have developed resistance to various antibacterial agents include *Acinetobacter, Escherichia coli, Pseudomonas aeruginosa, Staphylococcus aureus, Enterobacter, Klebsiella, Citrobacter* and a like.

In some other embodiments, there is provided a method for preventing or treating a bacterial infection in a subject, said infection is caused by bacteria producing Carbapenem hydrolyzing beta-lactamase enzymes, said method comprising administering to said subject: (a) aztreonam or a pharmaceutically acceptable derivative thereof, and (b) compound of Formula (I) or stereoisomer or a pharmaceutically acceptable derivative thereof.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

The synergistic killing effect of the combinations according to invention was studied by performing time kill studies. In a typical time kill study, the freshly grown cultures were diluted to the required cell density (initial starting inoculum) in Cation adjusted Muller Hinton broth medium (BD, USA).

The antibacterial agents (either alone or in combination) at the required concentrations were added into the culture-containing medium. The samples were incubated under shaking condition (120 rpm) at 37° C. Enumeration of viable bacterial count was done every 2 hour by diluting in normal saline and plating on to the Tryptic Soya Agar plates (BD, USA). The plates were incubated for 24 hours to arrive at the viable bacterial count. The results of these studies are summarized in Tables 1 and 2, wherein the antibacterial activity is expressed in terms of Log CFU (Colony Forming Units) per ml. In general, the decrease of 1 Log CFU/ml, corresponds to 90% killing of bacteria. Similarly, 2 Log CFU/ml reductions indicates to 99% killing of bacteria and 3 Log CFU/ml reductions is equal to 99.9% killing of bacteria. Ten compounds generally represented by a general Formula (I) were used and are as follows:

(a) Sodium salt of trans-7-oxo-6-sulphooxy-1,6-diazabicyclo[3.2.1]-octane-2-carbonitrile (Compound A)

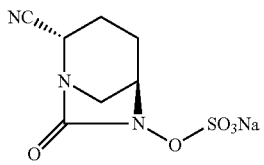

(b) trans-sulphuric acid mono-[2-(5-carboxamido)-[1,3,4]-oxadiazol-2-yl)-7-oxo-1,6-diazabicyclo[3.2.1]-octan-6-yl] ester (Compound B)

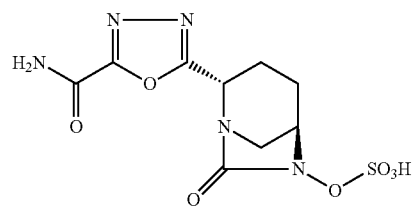 [SMILES: NC(=O)c1nnc([C@@H]2CC[C@@H]3CN2C(=O)N3OS(=O)(=O)O)o1]

(c) trans-sulphuric acid mono-[2-(5-(piperidin-4-yl)-[1,3,4]-oxadiazol-2-yl)-7-oxo-1,6-diazabicyclo[3.2.1]-octan-6-yl] ester (Compound C)

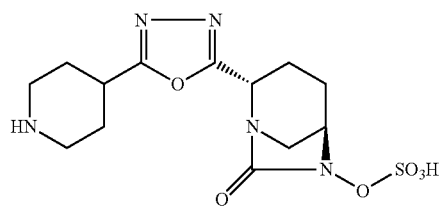 [SMILES: O=C1N2C[C@@H](CC[C@H]2c2nnc(C3CCNCC3)o2)N1OS(=O)(=O)O]

(d) trans-sulphuric acid mono-[2-(5-azetidin-3-ylmethyl-[1,3,4]-oxadiazol-2-yl)-7-oxo-1,6-diazabicyclo[3.2.1]-octan-6-yl] ester (Compound D)

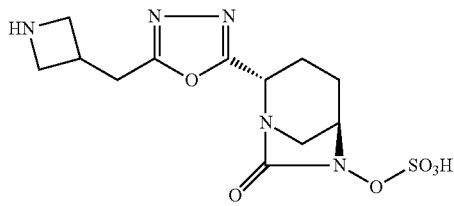 [SMILES: O=C1N2C[C@@H](CC[C@H]2c2nnc(CC3CNC3)o2)N1OS(=O)(=O)O]

(e) (2S,5R)-7-Oxo-6-sulphooxy-2-[N'—((R)-piperidine-3-carbonyl)-hydrazinocarbonyl]-1,6-diaza-bicyclo[3.2.1]octane (Compound E)

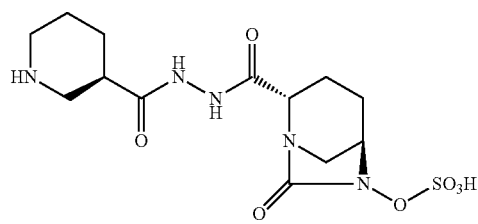 [SMILES: O=C(NNC(=O)[C@@H]1CC[C@@H]2CN1C(=O)N2OS(=O)(=O)O)[C@@H]1CCCNC1]

(f) (2S,5R)-7-Oxo-N-[(2S)-pyrrolidin-2-ylmethoxy]-6-(sulfooxy)-1,6-diaza bicyclo[3.2.1]octane-2-carboxamide (Compound F)

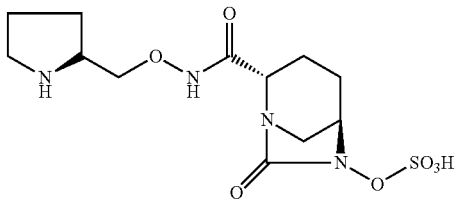

(g) (2S,5R)-7-Oxo-6-sulphooxy-2-[N'—((R)-pyrrolidine-3-carbonyl)-hydrazinocarbonyl]-1,6-diaza-bicyclo[3.2.1]octane (Compound G)

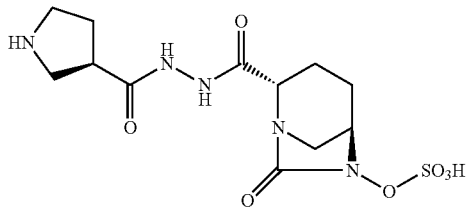 [SMILES: O=C(NNC(=O)[C@@H]1CC[C@@H]2CN1C(=O)N2OS(=O)(=O)O)[C@@H]1CCNC1]

(h) (2S,5R)-7-Oxo-N-[(2S)-piperidine-2-ylmethyloxy]-6-(sulfooxy)-1,6-diazabicyclo[3.2.1]octane-2-carboxamide (Compound H)

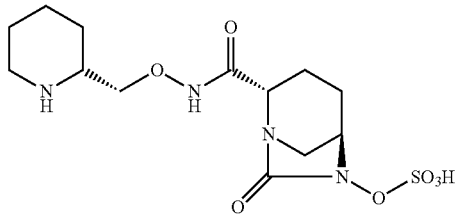

(i) trans-sulphuric acid mono-[2-(5-((S)-1-aminoethyl)-[1,3,4]-oxadiazol-2-yl)-7-oxo-1,6-diazabicyclo[3.2.1]-octan-6-yl] ester (Compound I); and

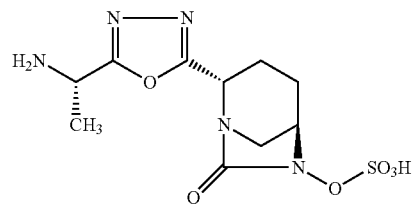 [SMILES: C[C@H](N)c1nnc([C@@H]2CC[C@@H]3CN2C(=O)N3OS(=O)(=O)O)o1]

(j) trans-sulphuric acid mono-[2-(5-((S)-pyrrolidin-2-yl)-[1,3,4]-oxadiazol-2-yl)-7-oxo-1,6-diazabicyclo[3.2.1]-octan-6-yl] ester (Compound J)

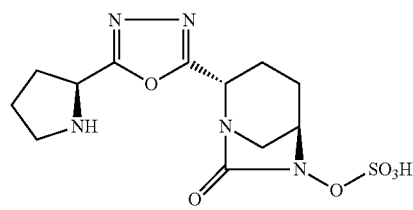 [SMILES: O=C1N2C[C@@H](CC[C@H]2c2nnc([C@@H]3CCCN3)o2)N1OS(=O)(=O)O]

Table 1 details the antibacterial activity of the combination according to invention against highly resistant *K. pneumoniae* NCTC 13443 strain producing multiple beta-lactamases such as SHV, TEM and carbapenem hydrolyzing metallo beta-lactamases (NDM-1). The assay without any antibacterial agent was taken as control. As can be seen from the Table 1; aztreonam, compound A, compound B, compound C, compound D, compound E, compound F, compound G, compound H, compound I, compound J and imipenem when used alone at 4 µg/ml, were not effective to decrease the bacterial count of *K. pneumoniae* throughout the duration of the study. However, surprisingly it has been observed that the combination of aztreonam and a compound selected from compound A, compound B, compound C, compound D, compound E, compound F, compound G, compound H, compound I or compound J, exhibited synergistic killing against a resistant strain of *K. pneumoniae*. The data reveals that combination of aztreonam (at 4 mcg/ml), and a compound selected from compound A, compound B, compound C, compound D, compound E, compound F, compound G, compound H, compound I or compound J (at 4 mcg/ml) significantly reduced bacterial count throughout the duration of the study considering 8 hours killing.

Table 2 details the antibacterial activity of the combination according to invention against highly resistant K. pneumoniae B 88 strain producing multiple beta-lactamases such as SHV, TEM, CTXM and carbapenem hydrolyzing metallo beta-lactamases (NDM-1). The assay without any antibacterial agent was taken as control. As can be seen from the Table 2; aztreonam, compound A, compound B, compound C, compound D, compound E, compound F, compound G, compound H, compound I, compound J and imipenem when used alone at 4 g/ml, were not effective to decrease the bacterial count of K. pneumoniae throughout the duration of the study. However, surprisingly it has been observed that the combination of aztreonam and a compound selected from compound A, compound B, compound C, compound D, compound E, compound F, compound G, compound H, compound I or compound J exhibited synergistic killing resistant strain of K. pneumoniae. The data reveals that for combination of aztreonam (at 4 mcg/ml) and a compound selected from compound A, compound B, compound C, compound D, compound E, compound F, compound G, compound H, compound I or compound J (at 4 mcg/ml) significantly reduced bacterial count throughout the duration of the study considering 8 hours killing.

The results given in the Tables 1 and 2, clearly and surprisingly demonstrate the potent antibacterial activity for the combination of aztreonam and representative compounds of Formula (I) against highly resistant strains of K. pneumoniae. Aztreonam and all the representative compounds of Formula (I) compounds, when used alone, were found to be ineffective against these resistant bacterial strains. However, the combination of aztreonam and compound of Formula (I) exhibited unusual and unexpected synergistic antibacterial effect against highly resistant bacterial strains. Thus combination of aztreonam and the compound of Formula (I) have tremendous beneficial effect in inhibiting highly resistant bacterial strains demonstrating the noteworthy therapeutic advance in the treatment of infections caused by such pathogens.

TABLE 1

Antibacterial activity of Aztreonam and representative compounds of Formula (I) (alone and in combination) against multi-drug resistant Klebsiella pneumoniae NCTC 13443 strain producing NDM-1, SHV and TEM beta-lactamase enzymes.

| Sr. | Combination | Bacterial count ($Log_{10}$CFU/ml) | | | | |
|---|---|---|---|---|---|---|
| | | 0 hours | 2 hours | 4 hours | 6 hours | 8 hours |
| 1. | Control (No active ingredient) | 7.5 | 8.4 | 9 | 9.35 | 9.53 |
| 2. | Aztreonam (4 mcg/ml) | 7.5 | 8.38 | 8.65 | 9.02 | 9.55 |
| 3. | Compound A (4 mcg/ml) | 7.5 | 8.3 | 8.5 | 8.8 | 9 |
| 4. | Compound B (4 mcg/ml) | 7.5 | 8.3 | 8.5 | 8.8 | 8.9 |
| 5. | Compound C (4 mcg/ml) | 7.5 | 8.2 | 8.9 | 9 | 9.5 |
| 6. | Compound D (4 mcg/ml) | 7.5 | 8.3 | 8.55 | 8.95 | 9.2 |
| 7. | Compound E (4 mcg/ml) | 7.5 | 8.35 | 8.6 | 8.8 | 8.9 |
| 8. | Compound F (4 mcg/ml) | 7.5 | 8.4 | 8.7 | 8.9 | 9.1 |
| 9. | Compound G (4 mcg/ml) | 7.5 | 8.36 | 8.78 | 8.9 | 9.2 |
| 10. | Compound H (4 mcg/ml) | 7.5 | 8.35 | 8.48 | 8.9 | 9.1 |
| 11. | Compound I (4 mcg/ml) | 7.5 | 8.36 | 8.79 | 8.9 | 9.1 |
| 12. | Compound J (4 mcg/ml) | 7.5 | 8.35 | 8.5 | 8.8 | 9.2 |
| 13. | Aztreonam (4 mcg/ml) + Compound A (4 mcg/ml) | 7.5 | 7.42 | 5.95 | 4.48 | 4.23 |
| 14. | Aztreonam (4 mcg/ml) + Compound B (4 mcg/ml) | 7.5 | 7.46 | 6.33 | 5.42 | 4.85 |
| 15. | Aztreonam (4 mcg/ml) + Compound C (4 mcg/ml) | 7.5 | 7.39 | 6.38 | 5.48 | 5.36 |
| 16. | Aztreonam (4 mcg/ml) + Compound D (4 mcg/ml) | 7.5 | 7.34 | 5.52 | 5.06 | 4.08 |
| 17. | Aztreonam (4 mcg/ml) + Compound E (4 mcg/ml) | 7.5 | 7.00 | 4.50 | 3.95 | 3.54 |
| 18. | Aztreonam (4 mcg/ml) + Compound F (4 mcg/ml) | 7.5 | 7.09 | 4.78 | 4.06 | 3.74 |
| 19. | Aztreonam (4 mcg/ml) + Compound G (4 mcg/ml) | 7.5 | 6.81 | 4.52 | 3.9 | 3.48 |
| 20. | Aztreonam (4 mcg/ml) + Compound H (4 mcg/ml) | 7.5 | 7.08 | 6.81 | 3.93 | 3.65 |
| 21. | Aztreonam (4 mcg/ml) + Compound I (4 mcg/ml) | 7.5 | 7.07 | 5.81 | 4.02 | 5.87 |
| 22. | Aztreonam (4 mcg/ml) + Compound J (4 mcg/ml) | 7.5 | 7.09 | 5.27 | 5.97 | 7.06 |
| 23. | Imipenem (4 mcg/ml) | 7.5 | 8.35 | 8.78 | 8.88 | 9.09 |

TABLE 2

Antibacterial activity of Aztreonam and representative compounds of Formula (I) (alone and in combination) against multi-drug resistant Klebsiella pneumoniae B 88 strain producing NDM-1, SHV, TEM and CTXM beta-lactamase enzymes.

| Sr. | Combination | Bacterial count ($Log_{10}$CFU/ml) | | | | |
|---|---|---|---|---|---|---|
| | | 0 hours | 2 hours | 4 hours | 6 hours | 8 hours |
| 1. | Control (No active ingredient) | 7.3 | 8.38 | 8.9 | 9.2 | 9.0 |
| 2 | Aztreonam (4 mcg/ml) | 7.3 | 8.16 | 8.7 | 8.88 | 9.04 |
| 3. | Compound A (4 mcg/ml) | 7.3 | 8 | 8.2 | 8.5 | 8.8 |
| 4. | Compound B (4 mcg/ml) | 7.3 | 7.98 | 8.2 | 8.50 | 8.9 |
| 5. | Compound C (4 mcg/ml) | 7.3 | 8.1 | 8.15 | 8.65 | 8.9 |
| 6. | Compound D (4 mcg/ml) | 7.3 | 8.05 | 8.3 | 8.7 | 8.8 |
| 7. | Compound E (4 mcg/ml) | 7.3 | 7.9 | 8.3 | 8.8 | 8.9 |
| 8. | Compound F (4 mcg/ml) | 7.3 | 8 | 8.2 | 8.35 | 8.7 |
| 9. | Compound G (4 mcg/ml) | 7.3 | 7.95 | 8.05 | 8.7 | 8.98 |
| 10. | Compound H (4 mcg/ml) | 7.3 | 8.15 | 8.3 | 8.65 | 8.98 |
| 11. | Compound I (4 mcg/ml) | 7.5 | 8.36 | 8.79 | 8.9 | 9.1 |
| 12. | Compound J (4 mcg/ml) | 7.5 | 8.35 | 8.5 | 8.8 | 9.2 |
| 13. | Aztreonam (4 mcg/ml) + Compound A (4 mcg/ml) | 7.3 | 7.15 | 6.28 | 5.27 | 6.02 |
| 14. | Aztreonam (4 mcg/ml) + Compound B (4 mcg/ml) | 7.3 | 5.95 | 6.08 | 4.48 | 4.48 |
| 15. | Aztreonam (4 mcg/ml) + Compound C (4 mcg/ml) | 7.3 | 6.34 | 5.45 | 4.78 | 4.65 |
| 16. | Aztreonam (4 mcg/ml) + Compound D (4 mcg/ml) | 7.3 | 6.08 | 4.85 | 4.04 | 3.85 |
| 17. | Aztreonam (4 mcg/ml) + Compound E (4 mcg/ml) | 7.3 | 4.74 | 4.18 | 3.65 | 3.4 |
| 18. | Aztreonam (4 mcg/ml) + Compound F (4 mcg/ml) | 7.3 | 5.9 | 5.08 | 4.98 | 4.88 |
| 19. | Aztreonam (4 mcg/ml) + Compound G (4 mcg/ml) | 7.3 | 5.8 | 5.0 | 4.74 | 4.42 |
| 20. | Aztreonam (4 mcg/ml) + Compound H (4 mcg/ml) | 7.3 | 4.6 | 4.04 | 3.4 | 3.3 |
| 21. | Aztreonam (4 mcg/ml) + Compound I (4 mcg/ml) | 7.3 | 6.87 | 5.38 | 4.23 | 4.92 |

TABLE 2-continued

Antibacterial activity of Aztreonam and representative compounds of Formula (I) (alone and in combination) against multi-drug resistant *Klebsiella pneumoniae* B 88 strain producing NDM-1, SHV, TEM and CTXM beta-lactamase enzymes.

| Sr. | Combination | Bacterial count ($Log_{10}$CFU/ml) | | | | |
|---|---|---|---|---|---|---|
| | | 0 hours | 2 hours | 4 hours | 6 hours | 8 hours |
| 22. | Aztreonam (4 mcg/ml) + Compound J (4 mcg/ml) | 7.3 | 6.92 | 5.33 | 4.04 | 4.25 |
| 23. | Imipenem (4 mcg/ml) | 7.3 | 8.28 | 8.7 | 8.9 | 9.2 |

The invention claimed is:

1. A pharmaceutical composition comprising: (a) aztreonam or a pharmaceutically acceptable salt thereof, and (b) a compound of Formula (I):

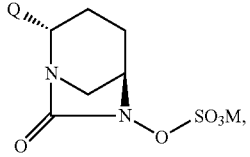

Formula (I)

or a stereoisomer or a pharmaceutically acceptable salt thereof;
wherein Q is
—CO—NH—NH—CO—$R_1$;
$R_1$ is
piperidine or pyrrolidine;
M is a hydrogen;
wherein the compound of Formula (I) or a stereoisomer or a pharmaceutically acceptable salt thereof is present in the composition in an amount from about 0.01 gram to about 8 grams per gram of aztreonam or a pharmaceutically acceptable salt thereof.

2. The pharmaceutical composition according to claim 1, wherein the compound of Formula (I) or stereoisomer or pharmaceutically acceptable salt thereof is present in the composition in an amount from about 0.01 gram to about 10 grams.

3. The pharmaceutical composition according to claim 1, wherein aztreonam or pharmaceutically acceptable salt thereof is present in the composition in an amount from about 0.01 gram to about 10 grams.

4. The pharmaceutical composition according to claim 1, comprising: (a) aztreonam or pharmaceutically acceptable salt thereof, and (b) the compound of Formula (I) or stereoisomer or pharmaceutically acceptable salt thereof, in any of the following amounts:

(i) about 0.25 gram of a compound of Formula (I) or stereoisomer or pharmaceutically acceptable salt thereof, and about 0.5 gram of aztreonam or pharmaceutically acceptable salt thereof;

(ii) about 0.5 gram of a compound of Formula (I) or stereoisomer or pharmaceutically acceptable salt thereof, and about 0.5 gram of aztreonam or pharmaceutically acceptable salt thereof;

(iii) about 1 gram of a compound of Formula (I) or stereoisomer or pharmaceutically acceptable salt thereof, and about 0.5 gram of aztreonam or pharmaceutically acceptable salt thereof;

(iv) about 2 grams of a compound of Formula (I) or stereoisomer or pharmaceutically acceptable salt thereof, and about 0.5 gram of aztreonam or pharmaceutically acceptable salt thereof;

(v) about 0.25 gram of a compound of Formula (I) or stereoisomer or pharmaceutically acceptable salt thereof, and about 1 gram of aztreonam or pharmaceutically acceptable salt thereof;

(vi) about 0.5 gram of a compound of Formula (I) or stereoisomer or pharmaceutically acceptable salt thereof, and about 1 gram of aztreonam or pharmaceutically acceptable salt thereof;

(vii) about 1 gram of a compound of Formula (I) or stereoisomer or pharmaceutically acceptable salt thereof, and about 1 gram of aztreonam or pharmaceutically acceptable salt thereof;

(viii) about 2 grams of a compound of Formula (I) or stereoisomer or pharmaceutically acceptable salt thereof, and about 1 gram of aztreonam or pharmaceutically acceptable salt thereof;

(ix) about 4 grams of a compound of Formula (I) or stereoisomer or pharmaceutically acceptable salt thereof, and about 1 gram of aztreonam or pharmaceutically acceptable salt thereof;

(x) about 2 grams of a compound of Formula (I) or stereoisomer or pharmaceutically acceptable salt thereof, and about 2 grams of aztreonam or pharmaceutically acceptable salt thereof; or (xi) about 1 gram of a compound of Formula (I) or stereoisomer or pharmaceutically acceptable salt thereof, and about 2 grams of aztreonam or pharmaceutically acceptable salt thereof.

5. The pharmaceutical composition according to claim 1, comprising (a) aztreonam or pharmaceutically acceptable salt thereof, and (b) (2S,5R)-7-Oxo-6-sulphooxy-2-[N'—((R)-piperidine-3-carbonyl)-hydrazinocarbonyl]-1,6-diazabicyclo[3.2.1]octane or stereoisomer or pharmaceutically acceptable salt thereof.

6. The pharmaceutical composition according to claim 1, comprising (a) aztreonam or a pharmaceutically acceptable salt thereof, and (b) (2S,5R)-7-Oxo-6-sulphooxy-2-[N'—((R)-pyrrolidine-3-carbonyl)-hydrazinocarbonyl]-1,6-diazabicyclo[3.2.1]octane or a stereoisomer or a pharmaceutically acceptable salt thereof.

7. The pharmaceutical composition according to claim 1, wherein the composition is in the form of a powder or a solution.

8. The pharmaceutical composition according to claim 7, wherein the composition is in the form of a powder or a solution that can be reconstituted by the addition of a compatible reconstitution diluent for use in parenteral administration or oral administration.

9. The pharmaceutical composition according to claim 1, for treating a bacterial infection.

10. A pharmaceutical composition comprising: (a) aztreonam or a pharmaceutically acceptable salt thereof, and (b) a compound of Formula (I):

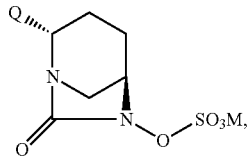

Formula (I)

or a stereoisomer or a pharmaceutically acceptable salt thereof;
wherein Q is CO—NH—NH—CO—$R_1$;
$R_1$ is piperidine or pyrrolidine;
M is hydrogen;
wherein (a) aztreonam or a pharmaceutically acceptable salt thereof, and (b) the compound of Formula (I) or a stereoisomer or a pharmaceutically acceptable salt thereof, are present in the composition in any of the following amounts:
(i) about 1 gram of a compound of Formula (I) or a stereoisomer or a pharmaceutically acceptable salt thereof, and about 1 gram of aztreonam or a pharmaceutically acceptable salt thereof;
(ii) about 2 grams of a compound of Formula (I) or a stereoisomer or a pharmaceutically acceptable salt thereof, and about 2 grams of aztreonam or a pharmaceutically acceptable salt thereof; or
(iii) about 1 gram of a compound of Formula (I) or a stereoisomer or a pharmaceutically acceptable salt thereof, and about 2 grams of aztreonam or a pharmaceutically acceptable salt thereof.

11. A method for treating a bacterial infection in a subject, said method comprising administering to said subject an effective amount of: (a) aztreonam or a pharmaceutically acceptable salt thereof, and (b) a compound of Formula (I) or a stereoisomer or a pharmaceutically acceptable salt thereof:

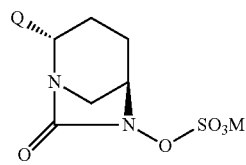

Formula (I)

wherein Q is
—CO—NH—NH—CO—$R_1$;
$R_1$ is
piperidine or pyrrolidine;
M is a hydrogen; wherein the amount of a compound of Formula (I) or a stereoisomer or a pharmaceutically acceptable salt thereof administered is from about 0.01 gram to about 8 gram per gram of aztreonam or a pharmaceutically acceptable salt thereof.

12. The method according to claim 11, wherein aztreonam or a pharmaceutically acceptable salt thereof, and the compound of Formula (I) or a stereoisomer or a pharmaceutically acceptable salt thereof, is administered in any of the following amounts:
(i) about 0.25 gram of a compound of Formula (I) or a stereoisomer or a pharmaceutically acceptable salt thereof, and about 0.5 gram of aztreonam or a pharmaceutically acceptable salt thereof;
(ii) about 0.5 gram of a compound of Formula (I) or a stereoisomer or a pharmaceutically acceptable salt thereof, and about 0.5 gram of aztreonam or a pharmaceutically acceptable salt thereof;
(iii) about 1 gram of a compound of Formula (I) or a stereoisomer or a pharmaceutically acceptable salt thereof, and about 0.5 gram of aztreonam or a pharmaceutically acceptable salt thereof;
(iv) about 2 gram of a compound of Formula (I) or a stereoisomer or a pharmaceutically acceptable salt thereof, and about 0.5 gram of aztreonam or a pharmaceutically acceptable salt thereof;
(v) about 0.25 gram of a compound of Formula (I) or a stereoisomer or a pharmaceutically acceptable salt thereof, and about 1 gram of aztreonam or a pharmaceutically acceptable salt thereof;
(vi) about 0.5 gram of a compound of Formula (I) or a stereoisomer or a pharmaceutically acceptable salt thereof, and about 1 gram of aztreonam or a pharmaceutically acceptable salt thereof;
(vii) about 1 gram of a compound of Formula (I) or a stereoisomer or a pharmaceutically acceptable salt thereof, and about 1 gram of aztreonam or a pharmaceutically acceptable salt thereof;
(viii) about 2 gram of a compound of Formula (I) or a stereoisomer or a pharmaceutically acceptable salt thereof, and about 1 gram of aztreonam or a pharmaceutically acceptable salt thereof;
(ix) about 4 gram of a compound of Formula (I) or a stereoisomer or a pharmaceutically acceptable salt thereof, and about 1 gram of aztreonam or a pharmaceutically acceptable salt thereof;
(x) about 2 gram of a compound of Formula (I) or a stereoisomer or a pharmaceutically acceptable salt thereof, and about 2 gram of aztreonam or a pharmaceutically acceptable salt thereof; or
(xi) about 1 gram of a compound of Formula (I) or a stereoisomer or a pharmaceutically acceptable salt thereof, and about 2 gram of aztreonam or a pharmaceutically acceptable salt thereof.

13. The method according to claim 11, wherein a compound of Formula (I) is selected from the following:
(e) (2S,5R)-7-Oxo-6-sulphooxy-2-[N'-((R)-piperidine-3-carbonyl)-hydrazinocarbonyl]-1,6-diaza-bicyclo[3.2.1]octane;
(g) (2S,5R)-7-Oxo-6-sulphooxy-2-[N'-((R)-pyrrolidine-3-carbonyl)-hydrazinocarbonyl]-1,6-diaza-bicyclo[3.2.1]octane;
or a stereoisomer thereof or a pharmaceutically acceptable salt thereof.

* * * * *